(12) United States Patent
Patel

(10) Patent No.: US 6,225,090 B1
(45) Date of Patent: May 1, 2001

(54) COMPOUNDS

(75) Inventor: Lisa Patel, London (GB)

(73) Assignees: SmithKline Beecham Corporation, Philadelphia, PA (US); SmithKline Beecham plc, Middlesex (GB)

( * ) Notice: Subject to any disclaimer, the term of this patent is extended or adjusted under 35 U.S.C. 154(b) by 0 days.

(21) Appl. No.: 09/552,351

(22) Filed: Apr. 19, 2000

(30) Foreign Application Priority Data

Apr. 19, 1999 (GB) .................................................. 9908897

(51) Int. Cl.[7] .............................. C12P 21/02; C12N 9/12; C12N 1/20; C12N 1/00; C07H 21/04
(52) U.S. Cl. .................... 435/69.2; 435/194; 435/252.3; 435/317.1; 435/320.1; 435/366; 536/23.5; 536/23.2
(58) Field of Search .................................... 435/194, 69.2, 435/252.3, 320.1, 366, 317.1; 536/23.2, 23.5

(56) References Cited

U.S. PATENT DOCUMENTS 5,856,132 * 1/1999 Stephens et al. .................... 435/69.2

OTHER PUBLICATIONS

Stephens, et al., "The Gβγ Sensitivity of a PI3K Is Dependent upon a Tightly Associated Adaptor, p101", Cell, vol. 89, pp. 105–114, (1997).
Krugmann, et al., "Characterizing the Interactions between the Two Subunits of the p101/p110y Phosphoinositide 3–Kinase and Their Role in the Activation of This Enzyme by Gβγ Subunits", The Journal of Biological Chemistry, vol. 274, pp. 17152–17158 (1999).
Maier, et al., "Roles of Non–catalytic Subunits in Gβγ–induced Activation of class I Phosphoinositide 3–Kinase Isoforms β and γ", The Journal of Biological Chemistry, vol. 274, pp. 29311–29317 (1999).
GenBank Accession No. AC002091, Hawkins, et al., Jul. 5, 1999 (Rel. 60, Last updated, Version 7).
GenBank Accession No. AC003695, Birren, et al., Oct. 31, 1998 (Rel. 57, Last updated, Version 30).

* cited by examiner

*Primary Examiner*—Elizabeth Slobodyansky
(74) *Attorney, Agent, or Firm*—William T. Han; Ratner & Presia; William T. King

(57) ABSTRACT

SVP4b polypeptides and polynucleotides and methods for producing such polypeptides by recombinant techniques are disclosed. Also disclosed are methods for utilizing SVP4b polypeptides and polynucleotides in therapy, and diagnostic assays for such.

9 Claims, No Drawings

SEQUENCE LISTING

<160> NUMBER OF SEQ ID NOS: 4

<210> SEQ ID NO 1
<211> LENGTH: 3006
<212> TYPE: DNA
<213> ORGANISM: HOMO SAPIENS

<400> SEQUENCE: 1

-continued

```
cccttccac ctctctgctc ccattcctga ccccttactt cccacacctc tgtcccgttc      60
tgctgcaggg gtgctctgtc ctgccactca gatgtggccc tccagatgcc attcctaccc    120
tggaggcagc tgtaaggccc ctggtcctgt ttccacagca cctgagctat agctgggctg    180
ggctgatcgc gctgcactgt gagcacctgt tgtctttact ggaccaggtg ctctctggga    240
aaggagctcg acaagctgac cggcgtctgt cccccatgca ggcgatgacc caggatgcag    300
ccagggccca cgacatgcac ggaggaccgc atccagcatg ccctggaacg ctgcctgcat    360
ggactcagcc tcagccgccg ctccacctcc tggtcagctg gctgtgtct gaactgctgg     420 agcctgcagg agctggtcag cagggacccg ggccacttcc ttatcctcct tgagcagatc    480
ctgcagaaga cccgagaggt ccaggagaag ggcacctacg acctgctcac ccgctggcc    540 ctgctcttct attccactgt tctttgtaca ccacacttcc caccagactc ggatctcctt    600
ctgaaggcag ccagcaccta ccaccggttc ctgacctggc ctgttcctta ctgcagcatc    660
tgccaggagc tgctcacctt cattgatgct gaactcaagg ccccaggtat ctcctaccag    720
agactggtga gggctgagca gggcctgccc atcaggagtc accgcagctc caccgtcacc    780
gtgctgctgc tgaacccagt ggaagtgcag gccgagttcc ttgctgtagc caataagctg    840
agtacgcccg acactcgcc tcacagtgcc tacaccaccc tgctcctgca cgccttccag    900
gccacctttg ggcccactg tgacgtcccg ggcctgcact gcaggctaca ggccaagacc    960
ctggcagagc ttgaggacat cttcacggag accgcagagg cacaggagct ggcatctggc   1020
atcggggatg ctgcagaggc ccggcggtgg ctcaggacca agctgcaggc gacactgcaa   1080
aaccagggaa gcttcatacc atccccatcc ctgtcgccag gtgctacacc tacagctgga   1140
gccaggacag ctttggagct gggcaccacc ccatgggagc cagagcaccaa tggcatctcc   1200 cactacctcg gcatgctgga cccctggtat gagcgcaatg tactgggcct catgcacctg   1260 cccctgaag tcctgtgcca gcagtccctg aaggctgaag cccaggccct ggagggctcc   1320
ccaacccagc tgcccatcct ggctgacatg ctactctact actgccgctt gccgccaga   1380 ccggtgctgc tgcaagtcta tcagaccgag ctgaccttca tcactgggga aagacgaca   1440 gagatcttca tccactcctt ggagctgggt cactccgctg ccacacgtgc catcaaggcg   1500
tcaggtcctg gcagcaagcg gctgggcatc gatggcgacc gggaggctgt tcctctaaca   1560
ctacagatta tttacagcca gggggccatc agtggacgaa gtcgctggag caacctggag   1620
aaggtctgta cctccgtgaa cctcaacaag gcctgccgga gcaggagga gctggattcc   1680 agcatggagg ccctgacgct aaacctgaca gaagtggtga aaaggcagaa ctccaaatcc   1740
aagaagggct ttaaccagat tagcacatcg cagatcaaag tggacaaggt gcagatcatc   1800
ggctccaaca gctgcccctt tgctgtgtgc ctggaccagg atgagagaaa gatcctgcag   1860
agtgtagtca gatgtgaggt ctcaccgtgc tacaagccag agaagagcga cctctcctca   1920 ccacccaga cgcctcctga cctgccggcc caggccgcac ctgatctctg ctccctcctc    1980
tgcctgccca tcatgacttt cagtggagct ctgccctagt gtgggcccag cgccagactg   2040
gacagaagcc ctgggtcat ttctccagca ctaaaatgga gtggagagtt ggggtggaaa   2100
taagacatcc ttaaaaggtt aaattgtctg caaagcacct agcccagtgc cgagctccca   2160
gtaggtgttc agtaaagctt agtgcctgac tttctgaaca ctgattcctc ctgtttggag   2220
tcactgggat actctcattg ccgttgggat gttcctcact ccttcccagt cgtggctga   2280 ggcagaaccc agactgaaga gggaagagac attccagagg aggattgcct tcgtcagggt   2340 aagggtggg ctgctcaggg gccctaccct tcacccccctt ctgtatcaga ttggccctcc   2400
```

-continued

```
cactcccatc tcactctgcg tgtacaatct tccatatccg caagttcact ggcactcttc    2460
tggcacctgg gcaagatccc agaacagagg atggagtgac tggcctcaca gagcttagtg    2520
cccgacactg gtgcatggga atggtcagc ctaggatagg acacgagagt ctgaaattca    2580
aagcaaccag cttgaagtgg tttgagaagc tggaagcaaa catgggctag agagataggg    2640
cagaagtcaa gacgaggatc tggactgatg tggagaaagt agccacggaa gcatgaactg    2700
tatcctgcac aaagtccctc ttccccgcct cctaattcat tatgcccaaa aggccttacg    2760
tgaaattcca gcccagagta ctcatgactt gagagacgtg gacagagcca gcttctacct    2820
tgcctggccg tctctcccct gtcttaatgt ctgctcttgc tctaagctcc agaagagtgg    2880
cgggccatgt atcttcaata tgtttttgct gtatgggcag gttgtcttat tatgtgatca    2940
acagatgtcc aggaactaat gagtggaatt taatattatt gtcaaataaa acttgatttg    3000
tcctat                                                              3006
```

<210> SEQ ID NO 2
<211> LENGTH: 574
<212> TYPE: PRT
<213> ORGANISM: HOMO SAPIENS

<400> SEQUENCE: 2

```
Met Gln Pro Gly Ala Thr Thr Cys Thr Glu Asp Arg Ile Gln His Ala
  1               5                  10                  15

Leu Glu Arg Cys Leu His Gly Leu Ser Leu Ser Arg Arg Ser Thr Ser
             20                  25                  30

Trp Ser Ala Gly Leu Cys Leu Asn Cys Trp Ser Leu Gln Glu Leu Val
         35                  40                  45

Ser Arg Asp Pro Gly His Phe Leu Ile Leu Leu Glu Gln Ile Leu Gln
     50                  55                  60

Lys Thr Arg Glu Val Gln Glu Lys Gly Thr Tyr Asp Leu Leu Thr Pro
 65                  70                  75                  80

Leu Ala Leu Leu Phe Tyr Ser Thr Val Leu Cys Thr Pro His Phe Pro
                 85                  90                  95

Pro Asp Ser Asp Leu Leu Leu Lys Ala Ala Ser Thr Tyr His Arg Phe
            100                 105                 110

Leu Thr Trp Pro Val Pro Tyr Cys Ser Ile Cys Gln Glu Leu Leu Thr
        115                 120                 125

Phe Ile Asp Ala Glu Leu Lys Ala Pro Gly Ile Ser Tyr Gln Arg Leu
    130                 135                 140

Val Arg Ala Glu Gln Gly Leu Pro Ile Arg Ser His Arg Ser Ser Thr
145                 150                 155                 160

Val Thr Val Leu Leu Leu Asn Pro Val Glu Val Gln Ala Glu Phe Leu
                165                 170                 175

Ala Val Ala Asn Lys Leu Ser Thr Pro Gly His Ser Pro His Ser Ala
            180                 185                 190

Tyr Thr Thr Leu Leu Leu His Ala Phe Gln Ala Thr Phe Gly Ala His
        195                 200                 205

Cys Asp Val Pro Gly Leu His Cys Arg Leu Gln Ala Lys Thr Leu Ala
    210                 215                 220

Glu Leu Glu Asp Ile Phe Thr Glu Thr Ala Glu Ala Gln Leu Ala
225                 230                 235                 240

Ser Gly Ile Gly Asp Ala Ala Glu Ala Arg Arg Trp Leu Arg Thr Lys
                245                 250                 255
```

```
Leu Gln Ala Thr Leu Gln Asn Gln Gly Ser Phe Ile Pro Ser Pro Ser
            260                 265                 270
Leu Ser Pro Gly Ala Thr Pro Thr Ala Gly Ala Arg Thr Ala Leu Glu
            275                 280                 285
Leu Gly Thr Thr Pro Trp Glu Glu Ser Thr Asn Gly Ile Ser His Tyr
            290                 295                 300
Leu Gly Met Leu Asp Pro Trp Tyr Glu Arg Asn Val Leu Gly Leu Met
305                 310                 315                 320
His Leu Pro Pro Glu Val Leu Cys Gln Gln Ser Leu Lys Ala Glu Ala
                325                 330                 335
Gln Ala Leu Glu Gly Ser Pro Thr Gln Leu Pro Ile Leu Ala Asp Met
                340                 345                 350
Leu Leu Tyr Tyr Cys Arg Phe Ala Ala Arg Pro Val Leu Leu Gln Val
                355                 360                 365
Tyr Gln Thr Glu Leu Thr Phe Ile Thr Gly Glu Lys Thr Thr Glu Ile
            370                 375                 380
Phe Ile His Ser Leu Glu Leu Gly His Ser Ala Ala Thr Arg Ala Ile
385                 390                 395                 400
Lys Ala Ser Gly Pro Gly Ser Lys Arg Leu Gly Ile Asp Gly Asp Arg
                405                 410                 415
Glu Ala Val Pro Leu Thr Leu Gln Ile Ile Tyr Ser Gln Gly Ala Ile
                420                 425                 430
Ser Gly Arg Ser Arg Trp Ser Asn Leu Glu Lys Val Cys Thr Ser Val
                435                 440                 445
Asn Leu Asn Lys Ala Cys Arg Lys Gln Glu Glu Leu Asp Ser Ser Met
            450                 455                 460
Glu Ala Leu Thr Leu Asn Leu Thr Glu Val Val Lys Arg Gln Asn Ser
465                 470                 475                 480
Lys Ser Lys Lys Gly Phe Asn Gln Ile Ser Thr Ser Gln Ile Lys Val
                485                 490                 495
Asp Lys Val Gln Ile Ile Gly Ser Asn Ser Cys Pro Phe Ala Val Cys
                500                 505                 510
Leu Asp Gln Asp Glu Arg Lys Ile Leu Gln Ser Val Val Arg Cys Glu
                515                 520                 525
Val Ser Pro Cys Tyr Lys Pro Glu Lys Ser Asp Leu Ser Ser Pro Pro
            530                 535                 540
Gln Thr Pro Pro Asp Leu Pro Ala Gln Ala Ala Pro Asp Leu Cys Ser
545                 550                 555                 560
Leu Leu Cys Leu Pro Ile Met Thr Phe Ser Gly Ala Leu Pro
                565                 570

<210> SEQ ID NO 3
<211> LENGTH: 3630
<212> TYPE: DNA
<213> ORGANISM: HOMO SAPIENS

<400> SEQUENCE: 3
atgcagccag ggccacgac  atgcacggag accgcatcc  agcatgccct ggaacgctgc      60
ctgcatggac tcagcctcag ccgccgctcc acctcctggt cagctgggct gtgtctgaac    120
tgctggagcc tgcaggagct ggtcagcagg gacccgggcc acttccttat cctccttgag    180
cagatcctgc agaagacccg agaggtccag gagaagggca cctacgacct gctcaccccg    240
ctggccctgc tcttctattc cactgttctt tgtacaccac acttcccacc agactcggat    300
ctccttctga aggcagccag cacctaccac cggttcctga cctggcctgt tccttactgc    360
```

-continued

```
agcatctgcc aggagctgct caccttcatt gatgctgaac tcaaggcccc agggatctcc    420
taccagagac tggtgagggc tgagcagggc ctgcccatca ggagtcaccg cagctccacc    480
gtcaccgtgc tgctgctgaa cccagtggaa gtgcaggccg agttccttgc tgtagccaat    540
aagctgagta cgcccggaca ctcgcctcac agtgcctaca ccaccctgct cctgcacgcc    600
ttccaggcca ccttcggggc ccactgtgac gtcccggccc tgcactgcag gctacaggcc    660
aagaccctgg cagagcttga ggacatcttc acggagaccg cagaggcaca ggagctggca    720
tctggcatcg gggatgctgc agaggccggg cggtggctca ggaccaagct gcaggcggtg    780
ggagaaaaag ctggcttccc tggggtgtta gacactgcaa aaccagggaa gcttcatacc    840
atccccatcc ctgtcgccag gtgctacacc tacagctgga ccaggacag cttgacatc     900
ctgcaggaaa tcctgctcaa ggaacaggag ctactccagc cagggatcct gggagatgat    960
gaagaggagg aagaggagga ggaggaggtg gaggaggact ggaaactga cgggcactgt   1020
gccgagagag attccctgct ctccaccagc tcttggcgt cccatgactc caccttgtcc    1080
cttgcatcct cccaggcctc gggcccggcc ctctcgcgcc atctgctgac ttcctttgtc   1140
tcaggcctct ctgatggcat ggacagcggc tacgtggagg acagcgagga gagctcctcc   1200
gagtggcctt ggaggcgtgg cagccaggaa cgccgaggcc accgcaggcc tgggcagaag   1260
ttcatcagga tctataaact cttcaagagc accagccagc tggtactgcg gagggactct   1320
cggagcctgg agggcagctc ggacacggcc ctgccctga ggcgggcagg gagcctctgc    1380
agcccctgg acgaaccagt atccccccct tcccgggccc agcgctcccg ctccctgccc    1440
cagcccaaac tcggtaccca gctgcccagc tggcttctgg ccctgcttc acgcccccag    1500
cgccgccgcc ccttcctgag tggagatgag gatcccaagg cttccacgct acgtgttgtg   1560
gtctttggct ccgatcggat ttcagggaag gtggctcggg cgtacagcaa ccttcggcgg   1620
ctggagaaca atcgcccact cctcacacgg ttcttcaaac ttcagttctt ctacgtgcct   1680
gtgaagcgaa gtcgtgggac cagccctggt gcctgtccac ccctcggag ccagacgccc   1740
tcacccccga cagactcccc taggcacgcc agccctggag agctgggcac cacccatgg    1800
gaggagagca ccaatggcat ctcccactac ctcggcatgc tggacccctg gtatgagcgc   1860
aatgtactgg gcctcatgca cctgccccct gaagtcctgt gccagcagtc cctgaaggct   1920
gaagcccagg ccctggaggg ctccccaacc cagctgccca tcctggctga catgctactc   1980
tactactgcc gcttttgccgc cagaccggtg ctgctgcaag tctatcagac cgagctgacc   2040
ttcatcactg gggagaagac gacagagatc ttcatccact ccttggagct gggtcactcc   2100
gctgccacac gtgccatcaa ggcgtcaggt cctggcagca agcggctggg catcgatggc   2160
gaccgggagg ctgttcctct aacactacag attatttaca gccaggggc catcagtgga   2220
cgaagtcgct ggagcaacct ggagaaggtc tgtacctccg tgaacctcaa caaggcctgc   2280
cggaagcagg aggagctgga ttccagcatg gaggccctga cgctaaacct gacagaagtg   2340
gtgaaaaggc agaactccaa atccaagaag gctttaaacc agattagcac atcgcagatc   2400
aaagtggaca aggtgcagat catcggctcc aacagctgcc cctttgctgt gtgcctggac   2460
caggatgaga gaaagatcct gcagagtgta gtcagatgtg aggtctcacc gtgctacaag   2520
ccagagaaga gcgacctctc ctcaccaccc cagacgcctc ctgacctgcc ggcccaggcc   2580
gcacctgatc tctgctccct cctctgcctg cccatcatga ctttcagtgg agctctgccc   2640
tagtgtgggc ccagcgccag actggacaga agccctgggg tcatttctcc agcactaaaa   2700
```

-continued

```
tggagtggag agttggggtg gaaataagac atccttaaaa ggttaaattg tctgcaaagc    2760
acctagccca gtgccgagct cccagtaggt gttcagtaaa gcttagtgcc tgactttctg    2820
aacactgatt cctcctgttt ggagtcactg ggatactctc attgccgttg ggatgttcct    2880
cactccttcc cagttcgtgg ctgaggcaga acccagactg aagagggaag agacattcca    2940
gaggaggatt gccttcgtca gggtaagggg tgggctgctc aggggcccta cccttcaccc    3000
ccttctgtat cagattggcc ctcccactcc catctcactc tgcgtgtaca atcttccata    3060
tccgcaagtt cactggcact cttctggcac ctgggcaaga tcccagaaca gaggatggag    3120
tgactggcct cacagagctt agtgcccgac actggtgcat gggaaatggt cagcctagga    3180
taggacacga gagtctgaaa ttcaaagcaa ccagcttgaa gtggtttgag aagctggaag    3240
caaacatggg ctagagagat agggcagaag tcaagacgag gatctggact gatgtggaga    3300
aagtagccac ggaagcatga actgtatcct gcacaaagtc cctcttcccc gcctcctaat    3360
tcattatgcc caaaaggcct tacgtgaaat tccagcccag agtactcatg acttgagaga    3420
cgtggacaga gccagcttct accttgcctg gccgtctctc ccctgtctta atgtctgctc    3480
ttgctctaag ctccagaaga gtggcgggcc atgtatcttc aatatgtttt tgctgtatgg    3540
gcaggttgtc ttattatgtg atcaacagat gtccaggaac taatgagtgg aatttaatat    3600
tattgtcaaa taaaacttga tttgtcctat                                    3630
```

<210> SEQ ID NO 4
<211> LENGTH: 880
<212> TYPE: PRT
<213> ORGANISM: HOMO SAPIENS

<400> SEQUENCE: 4

```
Met Gln Pro Gly Ala Thr Thr Cys Thr Glu Asp Arg Ile Gln His Ala
 1               5                   10                  15

Leu Glu Arg Cys Leu His Gly Leu Ser Leu Ser Arg Arg Ser Thr Ser
                20                  25                  30

Trp Ser Ala Gly Leu Cys Leu Asn Cys Trp Ser Leu Gln Glu Leu Val
            35                  40                  45

Ser Arg Asp Pro Gly His Phe Leu Ile Leu Leu Glu Gln Ile Leu Gln
        50                  55                  60

Lys Thr Arg Glu Val Gln Glu Lys Gly Thr Tyr Asp Leu Leu Thr Pro
 65                  70                  75                  80

Leu Ala Leu Leu Phe Tyr Ser Thr Val Leu Cys Thr Pro His Phe Pro
                85                  90                  95

Pro Asp Ser Asp Leu Leu Leu Lys Ala Ala Ser Thr Tyr His Arg Phe
            100                 105                 110

Leu Thr Trp Pro Val Pro Tyr Cys Ser Ile Cys Gln Glu Leu Leu Thr
        115                 120                 125

Phe Ile Asp Ala Glu Leu Lys Ala Pro Gly Ile Ser Tyr Gln Arg Leu
    130                 135                 140

Val Arg Ala Glu Gln Gly Leu Pro Ile Arg Ser His Arg Ser Thr
145                 150                 155                 160

Val Thr Val Leu Leu Asn Pro Val Glu Val Gln Ala Glu Phe Leu
                165                 170                 175

Ala Val Ala Asn Lys Leu Ser Thr Pro Gly His Ser Pro His Ser Ala
            180                 185                 190

Tyr Thr Thr Leu Leu Leu His Ala Phe Gln Ala Thr Phe Gly Ala His
        195                 200                 205
```

-continued

```
Cys Asp Val Pro Gly Leu His Cys Arg Leu Gln Ala Lys Thr Leu Ala
    210                 215                 220
Glu Leu Glu Asp Ile Phe Thr Glu Thr Ala Glu Ala Gln Glu Leu Ala
225                 230                 235                 240
Ser Gly Ile Gly Asp Ala Ala Glu Ala Arg Arg Trp Leu Arg Thr Lys
                245                 250                 255
Leu Gln Ala Val Gly Glu Lys Ala Gly Phe Pro Gly Val Leu Asp Thr
            260                 265                 270
Ala Lys Pro Gly Lys Leu His Thr Ile Pro Ile Pro Val Ala Arg Cys
        275                 280                 285
Tyr Thr Tyr Ser Trp Ser Gln Asp Ser Phe Asp Ile Leu Gln Glu Ile
    290                 295                 300
Leu Leu Lys Glu Gln Glu Leu Leu Gln Pro Gly Ile Leu Gly Asp Asp
305                 310                 315                 320
Glu Glu Glu Glu Glu Glu Glu Glu Val Glu Glu Asp Leu Glu Thr
                325                 330                 335
Asp Gly His Cys Ala Glu Arg Asp Ser Leu Leu Ser Thr Ser Ser Leu
                340                 345                 350
Ala Ser His Asp Ser Thr Leu Ser Leu Ala Ser Ser Gln Ala Ser Gly
            355                 360                 365
Pro Ala Leu Ser Arg His Leu Leu Thr Ser Phe Val Ser Gly Leu Ser
        370                 375                 380
Asp Gly Met Asp Ser Gly Tyr Val Glu Asp Ser Glu Glu Ser Ser Ser
385                 390                 395                 400
Glu Trp Pro Trp Arg Gly Ser Gln Glu Arg Arg Gly His Arg Arg
                405                 410                 415
Pro Gly Gln Lys Phe Ile Arg Ile Tyr Lys Leu Phe Lys Ser Thr Ser
            420                 425                 430
Gln Leu Val Leu Arg Arg Asp Ser Arg Ser Leu Glu Gly Ser Ser Asp
        435                 440                 445
Thr Ala Leu Pro Leu Arg Arg Ala Gly Ser Leu Cys Ser Pro Leu Asp
    450                 455                 460
Glu Pro Val Ser Pro Ser Arg Ala Gln Arg Ser Arg Ser Leu Pro
465                 470                 475                 480
Gln Pro Lys Leu Gly Thr Gln Leu Pro Ser Trp Leu Leu Ala Pro Ala
                485                 490                 495
Ser Arg Pro Gln Arg Arg Pro Phe Leu Ser Gly Asp Glu Asp Pro
            500                 505                 510
Lys Ala Ser Thr Leu Arg Val Val Phe Gly Ser Asp Arg Ile Ser
        515                 520                 525
Gly Lys Val Ala Arg Ala Tyr Ser Asn Leu Arg Arg Leu Glu Asn Asn
    530                 535                 540
Arg Pro Leu Leu Thr Arg Phe Phe Lys Leu Gln Phe Phe Tyr Val Pro
545                 550                 555                 560
Val Lys Arg Ser Arg Gly Thr Ser Pro Gly Ala Cys Pro Pro Arg
                565                 570                 575
Ser Gln Thr Pro Ser Pro Pro Thr Asp Ser Pro Arg His Ala Ser Pro
            580                 585                 590
Gly Glu Leu Gly Thr Thr Pro Trp Glu Glu Ser Thr Asn Gly Ile Ser
        595                 600                 605
His Tyr Leu Gly Met Leu Asp Pro Trp Tyr Glu Arg Asn Val Leu Gly
    610                 615                 620
Leu Met His Leu Pro Pro Glu Val Leu Cys Gln Gln Ser Leu Lys Ala
```

```
625                 630                 635                 640
Glu Ala Gln Ala Leu Glu Gly Ser Pro Thr Gln Leu Pro Ile Leu Ala
                645                 650                 655
Asp Met Leu Leu Tyr Tyr Cys Arg Phe Ala Ala Arg Pro Val Leu Leu
                660                 665                 670
Gln Val Tyr Gln Thr Glu Leu Thr Phe Ile Thr Gly Glu Lys Thr Thr
            675                 680                 685
Glu Ile Phe Ile His Ser Leu Glu Leu Gly His Ser Ala Ala Thr Arg
        690                 695                 700
Ala Ile Lys Ala Ser Gly Pro Gly Ser Lys Arg Leu Gly Ile Asp Gly
705                 710                 715                 720
Asp Arg Glu Ala Val Pro Leu Thr Leu Gln Ile Ile Tyr Ser Gln Gly
                725                 730                 735
Ala Ile Ser Gly Arg Ser Arg Trp Ser Asn Leu Glu Lys Val Cys Thr
                740                 745                 750
Ser Val Asn Leu Asn Lys Ala Cys Arg Lys Gln Glu Glu Leu Asp Ser
            755                 760                 765
Ser Met Glu Ala Leu Thr Leu Asn Leu Thr Glu Val Val Lys Arg Gln
        770                 775                 780
Asn Ser Lys Ser Lys Lys Gly Phe Asn Gln Ile Ser Thr Ser Gln Ile
785                 790                 795                 800
Lys Val Asp Lys Val Gln Ile Ile Gly Ser Asn Ser Cys Pro Phe Ala
                805                 810                 815
Val Cys Leu Asp Gln Asp Glu Arg Lys Ile Leu Gln Ser Val Val Arg
                820                 825                 830
Cys Glu Val Ser Pro Cys Tyr Lys Pro Glu Lys Ser Asp Leu Ser Ser
            835                 840                 845
Pro Pro Gln Thr Pro Pro Asp Leu Pro Ala Gln Ala Ala Pro Asp Leu
        850                 855                 860
Cys Ser Leu Leu Cys Leu Pro Ile Met Thr Phe Ser Gly Ala Leu Pro
865                 870                 875                 880
```

COMPOUNDS

FIELD OF THE INVENTION

This invention relates to newly identified polypeptides and polynucleotides encoding such polypeptides, to their use in therapy and in identifying compounds which may be agonists, antagonists and/or inhibitors which are potentially useful in therapy, and to production of such polypeptides and polynucleotides.

BACKGROUND OF THE INVENTION

The drug discovery process is currently undergoing a fundamental revolution as it embraces "functional genomics", that is, high throughput genome- or gene-based biology. This approach as a means to identify genes and gene products as therapeutic targets is rapidly superseding earlier approaches based on "positional cloning". A phenotype, that is a biological function or genetic disease, would be identified and this would then be tracked back to the responsible gene, based on its genetic map position.

Functional genomics relies heavily on high-throughput DNA sequencing technologies and the various tools of bioinformatics to identify gene sequences of potential interest from the many molecular biology databases now available. There is a continuing need to identify and characterise further genes and their related polypeptides/proteins, as targets for drug discovery.

SUMMARY OF THE INVENTION

The present invention relates to SVP4b, in particular SVP4b polypeptides and SVP4b polynucleotides, recombinant materials and methods for their production. In another aspect, the invention relates to methods for using such polypeptides and polynucleotides, including the treatment of disease states that involve leucocyte activation and infiltration including diseases such as arthritis, psoriasis, COPD and ARDS, hereinafter referred to as "the Diseases", amongst others. In a further aspect, the invention relates to methods for identifying agonists and antagonists/inhibitors using the materials provided by the invention, and treating conditions associated with SVP4b imbalance with the identified compounds. In a still further aspect, the invention relates to diagnostic assays for detecting diseases associated with inappropriate SVP4b activity or levels.

DESCRIPTION OF THE INVENTION

In a first aspect, the present invention relates to SVP4b polypeptides. Such peptides include isolated polypeptides comprising an amino acid sequence which has at least 95% identity, most preferably at least 97–99% identity, to that of SEQ ID NO:2 over the entire length of SEQ ID NO:2. Such polypeptides include those comprising the amino acid of SEQ ID NO:2.

Further peptides of the present invention include isolated polypeptides in which the amino acid sequence has at least 95% identity, most preferably at least 97–99% identity, to the amino acid sequence of SEQ ID NO:2 over the entire length of SEQ ID NO:2. Such polypeptides include the polypeptide of SEQ ID NO:2.

Further peptides of the present invention include isolated polypeptides encoded by a polynucleotide comprising the sequence contained in SEQ ID NO: 1.

Polypeptides of the present invention are believed to be members of the adaptor protein family of polypeptides. They are therefore of interest because they are involved in the generation of the important second messenger, phosphatidylinositol 3,4,5-triphosphate (PIP3); PIP3 is generated following the stimulation of various receptors and is involved, for example in leucocytes, in regulating chemotaxis, adherence and degranulation. PIP3 is primarily generated via the action of phosphatidylinositol 3-kinase, several of which are thought to exist however, one that appears to be particularly relevant in leucocytes is directly regulated, i.e. activated by G protein βγ subunits. Importantly, this regulation is dependent upon a novel adaptor protein, p101. Inhibition of this activation process by, for example, preventing Gβγ binding to p101 should prevent PIP3 accumulation. Such an action would be of benefit in various disease states that involve leucocyte activation and infiltration. These properties are hereinafter referred to as SVP4b activity" or SVP4b polypeptide activity" or "biological activity of SVP4b". Also included amongst these activities are antigenic and immunogenic activities of said SVP4b polypeptides, in particular the antigenic and immunogenic activities of the polypeptide of SEQ ID NO:2. Preferably, a polypeptide of the present invention exhibits at least one biological activity of SVP4b.

The polypeptides of the present invention may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

The present invention also includes include variants of the aforementioned polypeptides, that is polypeptides that vary from the referents by conservative amino acid substitutions, whereby a residue is substituted by another with like characteristics. Typical such substitutions are among Ala, Val, Leu and Ile; among Ser and Thr, among the acidic residues Asp and Glu; among Asn and Gln; and among the basic residues Lys and Arg; or aromatic residues Phe and Tyr. Particularly preferred are variants in which several, 5–10, 1–5, 1–3, 1–2 or 1 amino acids are substituted, deleted, or added in any combination.

Polypeptides of the present invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

In a further aspect, the present invention relates to SVP4b polynucleotides. Such polynucleotides include isolated polynucleotides comprising a nucleotide sequence encoding a polypeptide which has at least 95% identity to the amino acid sequence of SEQ ID NO:2, over the entire length of SEQ ID NO:2. In this regard, polypeptides which have at least 97% identity are highly preferred, whilst those with at least 98–99% identity are more highly preferred, and those with at least 99% identity are most highly preferred. Such polynucleotides include a polynucleotide comprising the nucleotide sequence contained in SEQ ID NO:1 encoding the polypeptide of SEQ ID NO:2.

Further polynucleotides of the present invention include isolated polynucleotides comprising a nucleotide sequence that has at least 95% identity to a nucleotide sequence encoding a polypeptide of SEQ ID NO:2, over the entire coding region. In this regard, polynucleotides which have at least 97% identity are highly preferred, whilst those with at least 98–99% identity are more highly preferred, and those with at least 99% identity are most highly preferred.

Further polynucleotides of the present invention include isolated polynucleotides comprising a nucleotide sequence which has at least 95% identity to SEQ ID NO:1 over the entire length of SEQ ID NO:1. In this regard, polynucleotides which have at least 97% identity are highly preferred, whilst those with at least 98–99% identity are more highly preferred, and those with at least 99% identity are most highly preferred. Such polynucleotides include a polynucleotide comprising the polynucleotide of SEQ ID NO:1 as well as the polynucleotide of SEQ ID NO:1.

The invention also provides polynucleotides which are complementary to all the above described polynucleotides.

The nucleotide sequence of SEQ ID NO:1 is a splice variant of the human p101 gene (EP0899328 SmithKline Beecham), which lacks exons 7b, 9 and 10. The polynucleotide of SEQ ID NO:1 is a cDNA sequence and comprises a polypeptide encoding sequence (nucleotide 296 to 2019) encoding a polypeptide of 575 amino acids, the polypeptide of SEQ ID NO:2. The nucleotide sequence encoding the polypeptide of SEQ ID NO:2 may be identical to the polypeptide encoding sequence contained in SEQ ID NO:1 or it may be a sequence other than the one contained in SEQ ID NO:1, which, as a result of the redundancy (degeneracy) of the genetic code, also encodes the polypeptide of SEQ ID NO:2.

Preferred polypeptides and polynucleotides of the present invention are expected to have, inter alia, similar biological functions/properties to their homologous polypeptides and polynucleotides. Furthermore, preferred polypeptides and polynucleotides of the present invention have at least one SVP4b activity.

Polynucleotides of the present invention may be obtained, using standard cloning and screening techniques, from a cDNA library derived from mRNA in cells of human peripheral blood leucocytes, (see for instance, Sambrook et al., Molecular Cloning: A Laboratory Manual, 2nd Ed., Cold Spring Harbor Laboratory Press, Cold Spring Harbor, N.Y. (1989)). Polynucleotides of the invention can also be obtained from natural sources such as genomic DNA libraries or can be synthesized using well known and commercially available techniques.

When polynucleotides of the present invention are used for the recombinant production of polypeptides of the present invention, the polynucleotide may include the coding sequence for the mature polypeptide, by itself; or the coding sequence for the mature polypeptide in reading frame with other coding sequences, such as those encoding a leader or secretory sequence, a pre-, or pro- or prepro- protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., Proc Natl Acad Sci USA (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Further embodiments of the present invention include polynucleotides encoding polypeptide variants which comprise the amino acid sequence of SEQ ID NO:2 and in which several, for instance from 5 to 10, 1 to 5, 1 to 3, 1 to 2 or 1, amino acid residues are substituted, deleted or added, in any combination.

Polynucleotides which are identical or sufficiently identical to a nucleotide sequence contained in SEQ ID NO:1, may be used as hybridization probes for cDNA and genomic DNA or as primers for a nucleic acid amplification (PCR) reaction, to isolate full-length cDNAs and genomic clones encoding polypeptides of the present invention and to isolate cDNA and genomic clones of other genes (including genes encoding homologs and orthologs from species other than human) that have a high sequence similarity to SEQ ID NO:1. Typically these nucleotide sequences are 70% identical, preferably 80% identical, more preferably 90% identical, most preferably 95% identical to that of the referent. The probes or primers will generally comprise at least 15 nucleotides, preferably, at least 30 nucleotides and may have at least 50 nucleotides. Particularly preferred probes will have between 30 and 50 nucleotides.

A polynucleotide encoding a polypeptide of the present invention, including homologs and orthologs from species other than human, may be obtained by a process which comprises the steps of screening an appropriate library under stringent hybridization conditions with a labeled probe having the sequence of SEQ ID NO:1 or a fragment thereof; and isolating full-length cDNA and genomic clones containing said polynucleotide sequence. Such hybridization techniques are well known to the skilled artisan. Preferred stringent hybridization conditions include overnight incubation at 42° C. in a solution comprising: 50% formamide, 5×SSC (150 mM NaCl, 15 nM trisodium citrate), 50 mM sodium phosphate (pH 7.6), 5×Denhardt's solution, 10% dextran sulfate, and 20 microgram/ml denatured, sheared salmon sperm DNA; followed by washing the filters in 0.1×SSC at about 65° C. Thus the present invention also includes polynucleotides obtainable by screening an appropriate library under stringent hybridization conditions with a labeled probe having the sequence of SEQ ID NO:1 or a fragment thereof.

The skilled artisan will appreciate that, in many cases, an isolated cDNA sequence will be incomplete, in that the region coding for the polypeptide is cut short at the 5' end of the cDNA. This is a consequence of reverse transcriptase, an enzyme with inherently low 'processivity' (a measure of the ability of the enzyme to remain attached to the template during the polymerisation reaction), failing to complete a DNA copy of the mRNA template during 1 st strand cDNA synthesis.

There are several methods available and well known to those skilled in the art to obtain full-length cDNAs, or extend short cDNAs, for example those based on the method of Rapid Amplification of cDNA ends (RACE) (see, for example, Frohman et al., PNAS USA 85, 8998–9002, 1988). Recent modifications of the technique, exemplified by the Marathon™" technology (Clontech Laboratories Inc.) for example, have significantly simplified the search for longer cDNAs. In the Marathon™ technology, cDNAs have been prepared from mRNA extracted from a chosen tissue and an 'adaptor' sequence ligated onto each end. Nucleic acid amplification (PCR) is then carried out to amplify the 'missing' 5' end of the cDNA using a combination of gene specific and adaptor specific oligonucleotide primers. The PCR reaction is then repeated using 'nested' primers, that is, primers designed to anneal within the amplified product (typically an adaptor specific primer that anneals further 3' in the adaptor sequence and a gene specific primer that anneals futher 5' in the known gene sequence). The products of this reaction can then be analyzed by DNA sequencing and a full-length cDNA constructed either by joining the product directly to the existing cDNA to give a complete sequence, or carrying out a separate full-length PCR using the new sequence information for the design of the 5' primer.

Recombinant polypeptides of the present invention may be prepared by processes well known in the art from genetically engineered host cells comprising expression systems. Accordingly, in a further aspect, the present invention relates to expression systems which comprise a polynucleotide or polynucleotides of the present invention, to host cells which are genetically engineered with such expression systems and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al, Basic Methods in Molecular Biology (1986) and Sambrook et al., Molecular Cloning: A Laboratory Manual, 2nd Ed., Cold Spring Harbor Laboratory Press, Cold Spring Harbor, N.Y. (1989). Preferred such methods include, for instance, calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as Streptococci, Staphylococci, *E. coli*, Streptomyces and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used, for instance, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector which is able to maintain, propagate or express a polynucleotide to produce a polypeptide in a host may be used. The appropriate nucleotide sequence may be inserted into an expression system by any of a variety of well-known and routine techniques, such as, for example, those set forth in Sambrook et al., Molecular Cloning, A Laboratory Manual (supra). Appropriate secretion signals may be incorporated into the desired polypeptide to allow secretion of the translated protein into the lumen of the endoplasmic reticulum, the periplasmic space or the extracellular environment. These signals may be endogenous to the polypeptide or they may be heterologous signals.

If a polypeptide of the present invention is to be expressed for use in screening assays, it is generally preferred that the polypeptide be produced at the surface of the cell. In this event, the cells may be harvested prior to use in the screening assay. If the polypeptide is secreted into the medium, the medium can be recovered in order to recover and purify the polypeptide. If produced intracellularly, the cells must first be lysed before the polypeptide is recovered.

Polypeptides of the present invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

This invention also relates to the use of polynucleotides of the present invention as diagnostic reagents. Detection of a mutated form of the gene characterized by the polynucleotide of SEQ ID NO:1 which is associated with a dysfunction will provide a diagnostic tool that can add to, or define, a diagnosis of a disease, or susceptibility to a disease, which results from under-expression, over-expression or altered expression of the gene. Individuals carrying mutations in the gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled SVP4b nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing (see, e.g., Myers et al., Science (1985) 230:1242). Sequence changes at specific locations may also be revealed by nuclease protection assays, such as RNase and S1 protection or the chemical cleavage method (see Cotton et al., Proc Natl Acad Sci USA (1985) 85: 4397–4401). In another embodiment, an array of oligonucleotides probes comprising SVP4b nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability (see for example: M. Chee et al., Science, Vol. 274, pp. 610–613 (1996)).

The diagnostic assays offer a process for diagnosing or determining a susceptibility to the Diseases through detection of mutation in the SVP4b gene by the methods described. In addition, such diseases may be diagnosed by methods comprising determining from a sample derived from a subject an abnormally decreased or increased level of polypeptide or mRNA. Decreased or increased expression can be measured at the RNA level using any of the methods well known in the art for the quantitation of polynucleotides, such as, for example, nucleic acid amplification, for instance PCR, RT-PCR, RNase protection, Northern blotting and other hybridization methods. Assay techniques that can be used to determine levels of a protein, such as a polypeptide of the present invention, in a sample derived from a host are well-known to those of skill in the art. Such assay methods include radioimmunoassays, competitive-binding assays, Western Blot analysis and ELISA assays.

Thus in another aspect, the present invention relates to a diagnostic kit which comprises:

(a) a polynucleotide of the present invention, preferably the nucleotide sequence of SEQ ID NO:1, or a fragment thereof;

(b) a nucleotide sequence complementary to that of (a);

(c) a polypeptide of the present invention, preferably the polypeptide of SEQ ID NO:2 or a fragment thereof; or (d) an antibody to a polypeptide of the present invention, preferably to the polypeptide of SEQ ID NO:2.

It will be appreciated that in any such kit, (a), (b), (c) or (d) may comprise a substantial component. Such a kit will be of use in diagnosing a disease or suspectability to a disease, particularly disease states that involve leucocyte activation and infiltration including diseases such as arthritis, psoriasis, COPD and ARDS, amongst others.

The nucleotide sequences of the present invention are also valuable for chromosome identification. The sequence is specifically targeted to, and can hybridize with, a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found in, for example, V. McKusick, Mendelian Inheritance in Man (available on-line through Johns Hopkins University Welch Medical Library). The relationship between genes and diseases that have been mapped to the same chromosomal region are then identified through linkage analysis (coinheritance of physically adjacent genes).

The differences in the cDNA or genomic sequence between affected and unaffected individuals can also be determined. If a mutation is observed in some or all of the affected individuals but not in any normal individuals, then the mutation is likely to be the causative agent of the disease.

The gene of the present invention maps to human chromosome 17p12–13.1.

The polypeptides of the invention or their fragments or analogs thereof, or cells expressing them, can also be used as immunogens to produce antibodies immunospecific for polypeptides of the present invention. The term "immunospecific" means that the antibodies have substantially greater affinity for the polypeptides of the invention than their affinity for other related polypeptides in the prior art.

Antibodies generated against polypeptides of the present invention may be obtained by administering the polypeptides or epitope-bearing fragments, analogs or cells to an animal, preferably a non-human animal, using routine protocols. For preparation of monoclonal antibodies, any technique which provides antibodies produced by continuous cell line cultures can be used. Examples include the hybridoma technique (Kohler, G. and Milstein, C., Nature (1975) 256:495–497), the trioma technique, the human B-cell hybridoma technique (Kozbor et al., Immunology Today (1983) 4:72) and the EBV-hybridoma technique (Cole et al., Monoclonal Antibodies and Cancer Therapy, 77–96, Alan R. Liss, Inc., 1985).

Techniques for the production of single chain antibodies, such as those described in U.S. Pat. No. 4,946,778, can also be adapted to produce single chain antibodies to polypeptides of this invention. Also, transgenic mice, or other organisms, including other mammals, may be used to express humanized antibodies.

The above-described antibodies may be employed to isolate or to identify clones expressing the polypeptide or to purify the polypeptides by affinity chromatography.

Antibodies against polypeptides of the present invention may also be employed to treat the Diseases, amongst others.

In a further aspect, the present invention relates to genetically engineered soluble fusion proteins comprising a polypeptide of the present invention, or a fragment thereof, and various portions of the constant regions of heavy or light chains of immunoglobulins of various subclasses (IgG, IgM, IgA, IgE). Preferred as an immunoglobulin is the constant part of the heavy chain of human IgG, particularly IgG1, where fusion takes place at the hinge region. In a particular embodiment, the Fc part can be removed simply by incorporation of a cleavage sequence which can be cleaved with blood clotting factor Xa. Furthermore, this invention relates to processes for the preparation of these fusion proteins by genetic engineering, and to the use thereof for drug screening, diagnosis and therapy. A further aspect of the invention also relates to polynucleotides encoding such fusion proteins. Examples of fusion protein technology can be found in International Patent Application Nos. WO94/29458 and WO94/22914.

Another aspect of the invention relates to a method for inducing an immunological response in a mammal which comprises inoculating the mammal with a polypeptide of the present invention, adequate to produce antibody and/or T cell immune response to protect said animal from the Diseases hereinbefore mentioned, amongst others. Yet another aspect of the invention relates to a method of inducing immunological response in a mammal which comprises, delivering a polypeptide of the present invention via a vector directing expression of the polynucleotide and coding for the polypeptide in vivo in order to induce such an immunological response to produce antibody to protect said animal from diseases.

A further aspect of the invention relates to an immunological/vaccine formulation (composition) which, when introduced into a mammalian host, induces an immunological response in that mammal to a polypeptide of the present invention wherein the composition comprises a polypeptide or polynucleotide of the present invention. The vaccine formulation may further comprise a suitable carrier. Since a polypeptide may be broken down in the stomach, it is preferably administered parenterally (for instance, subcutaneous, intramuscular, intravenous, or intradermal injection). Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Polypeptides of the present invention are responsible for many biological functions, including many disease states, in particular the Diseases hereinbefore mentioned. It is therefore desirous to devise screening methods to identify compounds which stimulate or which inhibit the function of the polypeptide. Accordingly, in a further aspect, the present invention provides for a method of screening compounds to identify those which stimulate or which inhibit the function of the polypeptide. In general, agonists or antagonists may be employed for therapeutic and prophylactic purposes for such Diseases as hereinbefore mentioned. Compounds may be identified from a variety of sources, for example, cells, cell-free preparations, chemical libraries, and natural product mixtures. Such agonists, antagonists or inhibitors so-identified may be natural or modified substrates, ligands, receptors, enzymes, etc., as the case may be, of the polypeptide; or may be structural or functional mimetics thereof (see Coligan et al., Current Protocols in Immunology 1(2):Chapter 5 (1991)).

The screening method may simply measure the binding of a candidate compound to the polypeptide, or to cells or membranes bearing the polypeptide, or a fusion protein thereof by means of a label directly or indirectly associated with the candidate compound. Alternatively, the screening method may involve competition with a labeled competitor. Further, these screening methods may test whether the candidate compound results in a signal generated by activation or inhibition of the polypeptide, using detection systems appropriate to the cells bearing the polypeptide. Inhibitors of activation are generally assayed in the presence of a known agonist and the effect on activation by the agonist by the presence of the candidate compound is observed. Constitutively active polypeptides may be employed in screening methods for inverse agonists or inhibitors, in the absence of an agonist or inhibitor, by testing whether the candidate compound results in inhibition of activation of the polypeptide. Further, the screening methods may simply comprise the steps of mixing a candidate compound with a solution containing a polypeptide of the present invention, to form a mixture, measuring SVP4b activity in the mixture, and comparing the SVP4b activity of the mixture to a standard. Fusion proteins, such as those made from Fc portion and SVP4b polypeptide, as hereinbefore described, can also be used for high-throughput screening assays to identify antagonists for the polypeptide of the present invention (see D. Bennett et al., J Mol Recognition, 8:52–58 (1995); and K. Johanson et al., J Biol Chem, 270(16):9459–9471 (1995)).

The polynucleotides, polypeptides and antibodies to the polypeptide of the present invention may also be used to configure screening methods for detecting the effect of added compounds on the production of mRNA and polypeptide in cells. For example, an ELISA assay may be constructed for measuring secreted or cell associated levels of polypeptide using monoclonal and polyclonal antibodies by standard methods known in the art. This can be used to discover agents which may inhibit or enhance the production of polypeptide (also called antagonist or agonist, respectively) from suitably manipulated cells or tissues.

The polypeptide may be used to identify membrane bound or soluble receptors, if any, through standard receptor binding techniques known in the art. These include, but are not limited to, ligand binding and crosslinking assays in which the polypeptide is labeled with a radioactive isotope (for instance, $^{125}$I), chemically modified (for instance, biotinylated), or fused to a peptide sequence suitable for detection or purification, and incubated with a source of the putative receptor (cells, cell membranes, cell supernatants, tissue extracts, bodily fluids). Other methods include biophysical techniques such as surface plasmon resonance and spectroscopy. These screening methods may also be used to identify agonists and antagonists of the polypeptide which compete with the binding of the polypeptide to its receptors, if any. Standard methods for conducting such assays are well understood in the art.

Examples of potential polypeptide antagonists include antibodies or, in some cases, oligonucleotides or proteins which are closely related to the ligands, substrates, receptors, enzymes, etc., as the case may be, of the polypeptide, e.g., a fragment of the ligands, substrates, receptors, enzymes, etc.; or small molecules which bind to the polypeptide of the present invention but do not elicit a response, so that the activity of the polypeptide is prevented.

Thus, in another aspect, the present invention relates to a screening kit for identifying agonists, antagonists, ligands, receptors, substrates, enzymes, etc. for polypeptides of the present invention; or compounds which decrease or enhance the production of such polypeptides, which comprises:

(a) a polypeptide of the present invention;

(b) a recombinant cell expressing a polypeptide of the present invention;

(c) a cell membrane expressing a polypeptide of the present invention; or (d) antibody to a polypeptide of the present invention;

which polypeptide is preferably that of SEQ ID NO:2.

It will be appreciated that in any such kit, (a), (b), (c) or (d) may comprise a substantial component.

It will be readily appreciated by the skilled artisan that a polypeptide of the present invention may also be used in a method for the structure-based design of an agonist, antagonist or inhibitor of the polypeptide, by:

(a) determining in the first instance the three-dimensional structure of the polypeptide;

(b) deducing the three-dimensional structure for the likely reactive or binding site(s) of an agonist, antagonist or inhibitor;

(c) synthezing candidate compounds that are predicted to bind to or react with the deduced binding or reactive site; and (d) testing whether the candidate compounds are indeed agonists, antagonists or inhibitors.

It will be further appreciated that this will normally be an interactive process.

In a further aspect, the present invention provides methods of treating abnormal conditions such as, for instance, disease states that involve leucocyte activation and infiltration including diseases such as arthritis, psoriasis, COPD and ARDS, related to either an excess of, or an under-expression of, SVP4b polypeptide activity.

If the activity of the polypeptide is in excess, several approaches are available. One approach comprises administering to a subject in need thereof an inhibitor compound (antagonist) as hereinabove described, optionally in combination with a pharmaceutically acceptable carrier, in an amount effective to inhibit the function of the polypeptide, such as, for example, by blocking the binding of ligands, substrates, receptors, enzymes, etc., or by inhibiting a second signal, and thereby alleviating the abnormal condition. In another approach, soluble forms of the polypeptides still capable of binding the ligand, substrate, enzymes, receptors, etc. in competition with endogenous polypeptide may be administered. Typical examples of such competitors include fragments of the SVP4b polypeptide.

In still another approach, expression of the gene encoding endogenous SVP4b polypeptide can be inhibited using expression blocking techniques. Known such techniques involve the use of antisense sequences, either internally generated or separately administered (see, for example, O'Connor, J Neurochem (1991) 56:560 in Oligodeoxynucleotides as Antisense Inhibitors of Gene Expression, CRC Press, Boca Raton, Fla. (1988)). Alternatively, oligonucleotides which form triple helices with the gene can be supplied (see, for example, Lee et al., Nucleic Acids Res (1979) 6:3073; Cooney et al., Science (1988) 241:456; Dervan et al., Science (1991) 251:1360). These oligomers can be administered per se or the relevant oligomers can be expressed in vivo.

For treating abnormal conditions related to an underexpression of SVP4b and its activity, several approaches are also available. One approach comprises administering to a subject a therapeutically effective amount of a compound which activates a polypeptide of the present invention, i.e., an agonist as described above, in combination with a pharmaceutically acceptable carrier, to thereby alleviate the abnormal condition. Alternatively, gene therapy may be employed to effect the endogenous production of SVP4b by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For an overview of gene therapy, see Chapter 20, Gene Therapy and other Molecular Geneticbased Therapeutic Approaches, (and references cited therein) in Human Molecular Genetics, T Strachan and A P Read, BIOS Scientific Publishers Ltd (1996). Another approach is to administer a therapeutic amount of a polypeptide of the present invention in combination with a suitable pharmaceutical carrier.

In a further aspect, the present invention provides for pharmaceutical compositions comprising a therapeutically effective amount of a polypeptide, such as the soluble form of a polypeptide of the present invention, agonist/antagonist peptide or small molecule compound, in combination with a pharmaceutically acceptable carrier or excipient. Such carriers include, but are not limited to, saline, buffered saline, dextrose, water, glycerol, ethanol, and combinations thereof. The invention further relates to pharmaceutical packs and kits comprising one or more containers filled with one or more of the ingredients of the aforementioned compositions of the invention. Polypeptides and other compounds of the present invention may be employed alone or in conjunction with other compounds, such as therapeutic compounds.

The composition will be adapted to the route of administration, for instance by a systemic or an oral route. Preferred forms of systemic administration include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if a polypeptide or other compounds of the present invention can be formulated in an enteric or an encapsulated formulation, oral administration may also be possible. Administration of these compounds may also be topical and/or localized, in the form of salves, pastes, gels, and the like.

The dosage range required depends on the choice of peptide or other compounds of the present invention, the route of administration, the nature of the formulation, the nature of the subject's condition, and the judgment of the attending practitioner. Suitable dosages, however, are in the range of 0.1–100 µg/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

Polynucleotide and polypeptide sequences form a valuable information resource with which to identify further sequences of similar homology. This is most easily facilitated by storing the sequence in a computer readable medium and then using the stored data to search a sequence database using well known searching tools, such as GCC. Accordingly, in a further aspect, the present invention provides for a computer readable medium having stored thereon a polynucleotide comprising the sequence of SEQ ID NO:1 and/or a polypeptide sequence encoded thereby.

The following definitions are provided to facilitate understanding of certain terms used frequently hereinbefore.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term "polynucleotide" also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications may occur anywhere in a polypeptide, including the peptide backbone, the amino acid side-chains and the amino or carboxyl termini. It will be appreciated that the same type of modification may be present to the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination (see, for instance, Proteins—Structure and Molecular Properties, 2nd Ed., T. E. Creighton, W. H. Freeman and Company, New York, 1993; Wold, F., Post-translational Protein Modifications: Perspectives and Prospects, pgs. 1–12 in Post-translational Covalent Modification of Proteins, B. C. Johnson, Ed., Academic Press, New York, 1983; Seifter et al., "Analysis for protein modifications and nonprotein cofactors", Meth Enzymol (1990) 182:626–646 and Rattan et al., "Protein Synthesis: Post-translational Modifications and Aging", Ann N.Y. Acad Sci (1992) 663:48–62).

"Variant" refers to a polynucleotide or polypeptide that differs from a reference polynucleotide or polypeptide, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., Nucleic Acids Research 12(1): 387 (1984)), BLASTP, BLASTN, and FASTA (Atschul, S. F. et al., J. Molec. Biol. 215: 403–410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215: 403–410 (1990). The well known Smith Waterman algorithm may also be used to determine identity.

Preferred parameters for polypeptide sequence comparison include the following:
1) Algorithm: Needleman and Wunsch, J. Mol Biol. 48: 443–453 (1970)
Comparison matrix: BLOSSUM62 from Hentikoff and Hentikoff, Proc. Natl. Acad. Sci. USA. 89:10915–10919 (1992)
Gap Penalty: 12
Gap Length Penalty: 4
A program useful with these parameters is publicly available as the "gap" program from Genetics Computer Group, Madison Wis. The aforementioned parameters are the default parameters for peptide comparisons (along with no penalty for end gaps).

Preferred parameters for polynucleotide comparison include the following:
1) Algorithm: Needleman and Wunsch, J. Mol Biol. 48: 443–453 (1970)
Comparison matrix: matches=+10, mismatch=0
Gap Penalty: 50
Gap Length Penalty: 3
Available as: The "gap" program from Genetics Computer Group, Madison Wis. These are the default parameters for nucleic acid comparisons.

By way of example, a polynucleotide sequence of the present invention may be identical to the reference sequence of SEQ ID NO:1, that is be 100% identical, or it may include up to a certain integer number of nucleotide alterations as compared to the reference sequence. Such alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in SEQ ID NO:1 by the numerical percent of the respective percent identity (divided by 100) and subtracting that product from said total number of nucleotides in SEQ ID NO:1, or:

$$n_n \leq x_n - (x_n \cdot y),$$

wherein $n_n$ is the number of nucleotide alterations, $x_n$ is the total number of nucleotides in SEQ ID NO:1, and y is, for instance, 0.70 for 70%, 0.80 for 80%, 0.85 for 85%, 0.90 for 90%, 0.95 for 95%, etc., and wherein any non-integer product of $x_n$ and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

Similarly, a polypeptide sequence of the present invention may be identical to the reference sequence of SEQ ID NO:2, that is be 100% identical, or it may include up to a certain integer number of amino acid alterations as compared to the reference sequence such that the % identity is less than 100%. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO:2 by the numerical percent of the respective percent identity (divided by 100) and then subtracting that product from said total number of amino acids in SEQ ID NO:2, or:

$$n_a \leq x_a - (x_a \cdot y),$$

wherein $n_a$ is the number of amino acid alterations, $x_a$ is the total number of amino acids in SEQ ID NO:2, and y is, for instance 0.70 for 70%, 0.80 for 80%, 0.85 for 85% etc., and wherein any non-integer product of $x_a$ and y is rounded down to the nearest integer prior to subtracting it from $x_a$.

"Homolog" is a generic term used in the art to indicate a polynucleotide or polypeptide sequence possessing a high degree of sequence relatedness to a reference sequence. Such relatedness may be quantified by determining the degree of identity and/or similarity between the two sequences as hereinbefore defined. Falling within this generic term are the terms "ortholog", and "paralog". "Ortholog" refers to a polynucleotide or polypeptide that is the functional equivalent of the polynucleotide or polypeptide in another species. "Paralog" refers to a polynucleotideor polypeptide that within the same species which is functionally similar.

"Fusion protein" refers to a protein encoded by two, often unrelated, fused genes or fragments thereof. In one example, EP-A-0 464 discloses fusion proteins comprising various portions of constant region of immunoglobulin molecules together with another human protein or part thereof. In many cases, employing an immunoglobulin Fc region as a part of a fusion protein is advantageous for use in therapy and diagnosis resulting in, for example, improved pharmacokinetic properties [see, e.g., EP-A 0232 262]. On the other hand, for some uses it would be desirable to be able to delete the Fc part after the fusion protein has been expressed, detected and purified.

All publications, including but not limited to patents and patent applications, cited in this specification are herein incorporated by reference as if each individual publication were specifically and individually indicated to be incorporated by reference herein as though fully set forth.

EXAMPLE

The incorporation of $^{32}$P into phosphatidylinositol-4,5-bisphosphate (PIP2) to create phosphatidylinositol-3,4,5-triphosphate (PIP3) was analysed. In brief, GFP-fusion tagged p110gamma (a phosphatidylinositol-3-kinase (PI3K)) and SVP4b, and GFP-fusion tagged p110gamma and full length p101 were co-expressed in SF21 cells. Incorporation if $^{32}$P into PIP3 was then assessed in the presence/absence of G-protein beta/gamma subunits (Gβγ) (which have been shown in the past to bind to the p101g/p101 heterodimer to stimulate kinase activity, Stephens et al. (1997), Cell 89 pp. 105–114). In the absence of Gβγ, the level of $^{32}$P incorporation into PIP3 caused by SVP4b was reduced by 62.7% compared with the stimulation seen with full length p101. In the presence of Gβγ, a 9.4 fold stimulation of $^{32}$P incorporation into PIP3 over that seen in the absence of Gβγ was seen with the p110g/SVP4b heterodimer whilst the p110g/p101 heterodimer produced a 4.6 fold stimulation over basal activity in the presence of Gβγ.

Data:

Figures are in pmol incorporation of $^{32}$P into PIP3

|  | Heterodimer | |
|---|---|---|
|  | p110g/p101 | p110g/SVP4b |
| No Gβγ | 1.089 | 2.918 |
| Plus Gβγ | 10.291 | 13.48 |
| Fold stimulation | 9.4 | 4.6 |

SEQUENCE INFORMATION

SEQ ID NO:1 - SVP-4b (lacks exons 7b ,9 and 10)

CCCTTTCCACCTCTCTGCTCCCATTCCTGACCCCTTACTTCCCACACCTCTGTCCCGTTCTGCTGCAGGGGT

GCTCTGTCCTGCCACTCAGATGTGGCCCTCCAGATGCCATTCCTACCCTGGAGGCAGCTGTAAGGCCCCTGG

TCCTGTTTCCACAGCACCTGAGCTATAGCTGGGCTGGGCTGATCGCGCTGCACTGTGAGCACCTGTTGTCTT

TACTGGACCAGGTGCTCTCTGGGAAAGGAGCTCGACAAGCTGACCGGCGTCTGTCCCCATGCAGGCGATGA

-continued

```
CCCAGGATGCAGCCAGGGGCCACGACATGCACGGAGGACCGCATCCAGCATGCCCTGGAACGCTGCCTGCAT
GGACTCAGCCTCAGCCGCCGCTCCACCTCCTGGTCAGCTGGGCTGTGTCTGAACTGCTGGAGCCTGCAGGAG
CTGGTCAGCAGGGACCCGGGCCACTTCCTTATCCTCCTTGAGCAGATCCTGCAGAAGACCCGAGAGGTCCAG
GAGAAGGGCACCTACGACCTGCTCACCCCGCTGGCCCTGCTCTTCTATTCCACTGTTCTTTGTACACCACAC
TTCCCACCAGACTCGGATCTCCTTCTGAAGGCAGCCAGCACCTACCACCGGTTCCTGACCTGGCCTGTTCCT
TACTGCAGCATCTGCCAGGAGCTGCTCACCTTCATTGATGCTGAACTCAAGGCCCCAGGTATCTCCTACCAG
AGACTGGTGAGGGCTGAGCAGGGCCTGCCCATCAGGAGTCACCGCAGCTCCACCGTCACCGTGCTGCTGCTG
AACCCAGTGGAAGTGCAGGCCGAGTTCCTTGCTGTAGCCAATAAGCTGAGTACGCCCGGACACTCGCCTCAC
AGTGCCTACACCACCCTGCTCCTGCACGCCTTCCAGGCCACCTTTGGGGCCCACTGTGACGTCCCGGGCCTG
CACTGCAGGCTACAGGCCAAGACCCTGGCAGAGCTTGAGGACATCTTCACGGAGACCGCAGAGGCACAGGAG
CTGGCATCTGGCATCGGGGATGCTGCAGAGGCCCGGCGGTGGCTCAGGACCAAGCTGCAGGCGACACTGCAA
AACCAGGGAAGCTTCATACCATCCCCATCCCTGTCGCCAGGTGCTACACCTACAGCTGGAGCCAGGACAGCT
TTGGAGCTGGGCACCACCCCATGGGAGGAGAGCACCAATGGCATCTCCCACTACCTCGGCATGCTGGACCCC
TGGTATGAGCGCAATGTACTGGGCCTCATGCACCTGCCCCCTGAAGTCCTGTGCCAGCAGTCCCTGAAGGCT
GAAGCCCAGGCCCTGGAGGGCTCCCCAACCCAGCTGCCCATCCTGGCTGACATGCTACTCTACTACTGCCGC
TTTGCCGCCAGACCGGTGCTGCTGCAAGTCTATCAGACCGAGCTGACCTTCATCACTGGGGAGAAGACGACA
GAGATCTTCATCCACTCCTTGGAGCTGGGTCACTCCGCTGCCACACGTGCCATCAAGGCGTCAGGTCCTGGC
AGCAAGCGGCTGGGCATCGATGGCGACCGGGAGGCTGTTCCTCTAACACTACAGATTATTTACAGCCAGGGG
GCCATCAGTGGACGAAGTCGCTGGAGCAACCTGGAGAAGGTCTGTACCTCCGTGAACCTCAACAAGGCCTGC
CGGAAGCAGGAGGAGCTGGATTCCAGCATGGAGGCCCTGACGCTAAACCTGACAGAAGTGGTGAAAAGGCAG
AACTCCAAATCCAAGAAGGGCTTTAACCAGATTAGCACATCGCAGATCAAAGTGGACAAGGTGCAGATCATC
GGCTCCAACAGCTGCCCCTTTGCTGTGTGCCTGGACCAGGATGAGAGAAAGATCCTGCAGAGTGTAGTCAGA
TGTGAGGTCTCACCGTGCTACAAGCCAGAGAAGAGCGACCTCTCCTCACCACCCCAGACGCCTCCTGACCTG
CCGGCCCAGGCCGCACCTGATCTCTGCTCCCTCCTCTGCCTGCCCATCATGACTTTCAGTGGAGCTCTGCCC
TAGTGTGGGCCCAGCGCCAGACTGGACAGAAGCCCTGGGGTCATTTCTCCAGCACTAAAATGGAGTGGAGAG
TTGGGGTGGAAATAAGACATCCTTAAAAGGTTAAATTGTCTGCAAAGCACCTAGCCCAGTGCCGAGCTCCCA
GTAGGTGTTCAGTAAAGCTTAGTGCCTGACTTTCTGAACACTGATTCCTCCTGTTTGGAGTCACTGGGATAC
TCTCATTGCCGTTGGGATGTTCCTCACTCCTTCCCAGTTCGTGGCTGAGGCAGAACCCAGACTGAAGAGGGA
AGAGACATTCCAGAGGAGGATTGCCTTCGTCAGGGTAAGGGGTGGGCTGCTCAGGGGCCCTACCCTTCACCC
CCTTCTGTATCAGATTGGCCCTCCCACTCCCATCTCACTCTGCGTGTACAATCTTCCATATCCGCAAGTTCA
CTGGCACTCTTCTGGCACCTGGGCAAGATCCCAGAACAGAGGATGGAGTGACTGGCCTCACAGAGCTTAGTG
CCCGACACTGGTGCATGGGAAATGGTCAGCCTAGGATAGGACACGAGAGTCTGAAATTCAAAGCAACCAGCT
TGAAGTGGTTTGAGAAGCTGGAAGCAAACATGGGCTAGAGAGATAGGGCAGAAGTCAAGACGAGGATCTGGA
CTGATGTGGAGAAAGTAGCCACGGAAGCATGAACTGTATCCTGCACAAAGTCCCTCTTCCCCGCCTCCTAAT
TCATTATGCCCAAAAGGCCTTACGTGAAATTCCAGCCCAGAGTACTCATGACTTGAGAGACGTGGACAGAGC
CAGCTTCTACCTTGCCTGGCCGTCTCTCCCCTGTCTTAATGTCTGCTCTTGCTCTAAGCTCCAGAAGAGTGG
CGGGCCATGTATCTTCAATATGTTTTTGCTGTATGGGCAGGTTGTCTTATTATGTGATCAACAGATGTCCAG
GAACTAATGAGTGGAATTTAATATTATTGTCAAATAAAACTTGATTTGTCCTAT
```

SEQ ID NO:2 - SVP-4b protein

MQPGATTCTEDRIQHALERCLHGLSLSRRSTSWSAGLCLNCWSLQELVSRDPGHFLILLEQILQKTREVQEK

-continued

GTYDLLTPLALLFYSTVLCTPHFPPDSDLLLKAASTYHRFLTWPVPYCSICQELLTFIDAELKAPGISYQRL

VRAEQGLPIRSHRSSTVTVLLLNPVEVQAEFLAVANKLSTPGHSPHSAYTTLLLHAFQATFGAHCDVPGLHC

RLQAKTLAELEDIFTETAEAQELASGIGDAAEARRWLRTKLQATLQNQGSFIPSPSLSPGATPTAGARTALE

LGTTPWEESTNGISHYLGMLDPWYERNVLGLMHLPPEVLCQQSLKAEAQALEGSPTQLPILADMLLYYCRFA

ARPVLLQVYQTELTFITGEKTTEIFIHSLELGHSAATRAIKASGPGSKRLGIDGDREAVPLTLQIIYSQGAI

SGRSRWSNLEKVCTSVNLNKACRKQEELDSSMEALTLNLTEVVKRQNSKSKKGFNQISTSQIKVDKVQIIGS

NSCPFAVCLDQDERKILQSVVRCEVSPCYKPEKSDLSSPPQTPPDLPAQAAPDLCSLLCLPIMTFSGALP

SEQ ID NO:3 - full length p 101

ATGCAGCCAGGGGCCACGACATGCACGGAGGACCGCATCCAGCATGCCCTGGAACGCTGCCTGCATGGACTCA

GCCTCAGCCGCCGCTCCACCTCCTGGTCAGCTGGGCTGTGTCTGAACTGCTGGACCTGCAGGAGCTGGTCAG

CAGGGACCCGGGCCACTTCCTTATCCTCCTTGAGCAGATCCTGCAGAAGACCCGAGAGGTCCAGGAGAAGGGC

ACCTACGACCTGCTCACCCCGCTGGCCCTGCTCTTCTATTCCACTGTTCTTTGTACACCACACTTCCCACCAG

ACTCGGATCTCCTTCTGAAGGCAGCCAGCACCTACCACCGGTTCCTGACCTGGCCTGTTCCTTACTGCAGCAT

CTGCCAGGAGCTGCTCACCTTCATTGATGCTGAACTCAAGGCCCCAGGGATCTCCTACCAGAGACTGGTGAGG

GCTGAGCAGGGCCTGCCCATCAGGAGTCACCGCAGCTCCACCGTCACCGTGCTGCTGCTGAACCCAGTGGAAG

TGCAGGCCGAGTTCCTTGCTGTAGCCAATAAGCTGAGTACGCCCGGACACTCGCCTCACAGTGCCTACACCAC

CCTGCTCCTGCACGCCTTCCAGGCCACCTTTGGGGCCCACTGTGACGTCCCGGGCCTGCACTGCAGGCTACAG

GCCAAGACCCTGGCAGAGCTTGAGGACATCTTCACGGAGACCGCAGAGGCACAGGAGCTGGCATCTGGCATCG

GGGATGCTGCAGAGGCCCGGCGGTGGCTCAGGACCAAGCTGCAGGCGGTGGGAGAAAAAGCTGGCTTCCCTGG

GGTGTTAGACACTGCAAAACCAGGGAAGCTTCATACCATCCCCATCCCTGTCGCCAGGTGCTACACCTACAGC

TGGAGCCAGGACAGCTTTGACATCCTGCAGGAAATCCTGCTCAAGGAACAGGAGCTACTCCAGCCAGGGATCC

TGGGAGATGATGAAGAGGAGGAAGAGGAGGAGGAGGAGGTGGAGGAGGACTTGGAAACTGACGGGCACTGTGC

CGAGAGAGATTCCCTGCTCTCCACCAGCTCTTTGGCGTCCCATGACTCCACCTTGTCCCTTGCATCCTCCCAG

GCCTCGGGGCCGGCCCTCTCGCGCCATCTGCTGACTTCCTTTGTCTCAGGCCTCTCTGATGGCATGGACAGCG

GCTACGTGGAGGACAGCGAGGAGAGCTCCTCCGAGTGGCCTTGGAGGCGTGGCAGCCAGGAACGCCGAGGCCA

CCGCAGGCCTGGGCAGAAGTTCATCAGGATCTATAAACTCTTCAAGAGCACCAGCCAGCTGGTACTGCGGAGG

GACTCTCGGAGCCTGGAGGGCAGCTCGGACACGGCCCTGCCCCTGAGGCGGGCAGGGAGCCTCTGCAGCCCCC

TGGACGAACCAGTATCACCCCCTTCCCGGGCCCAGCGCTCCCGCTCCCTGCCCCAGCCCAAACTCGGTACCCA

GCTGCCCAGCTGGCTTCTGGCCCCTGCTTCACGCCCCCAGCGCCGCCGCCCCTTCCTGAGTGGAGATGAGGAT

CCCAAGGCTTCCACGCTACGTGTTGTGGTCTTTGGCTCCGATCGGATTTCAGGGAAGGTGGCTCGGGCGTACA

GCAACCTTCGGCGGCTGGAGAACAATCGCCCACTCCTCACACGGTTCTTCAAACTTCAGTTCTTCTACGTGCC

TGTGAAGCGAAGTCGTGGGACCAGCCCTGGTGCCTGTCCACCCCCTCGGAGCCAGACGCCCTCACCCCCGACA

GACTCCCCTAGGCACGCCAGCCCTGGAGAGCTGGGCACCACCCCATGGGAGGAGAGCACCAATGGCATCTCCC

ACTACCTCGGCATGCTGGACCCCTGGTATGAGCGCAATGTACTGGGCCTCATGCACCTGCCCCCTGAAGTCCT

GTGCCAGCAGTCCCTGAAGGCTGAAGCCCAGGCCCTGGAGGGCTCCCCAACCCAGCTGCCCATCCTGGCTGAC

ATGCTACTCTACTACTGCCGCTTTGCCGCCAGACCGGTGCTGCTGCAAGTCTATCAGACCGAGCTGACCTTCA

TCACTGGGGAGAAGACGACAGAGATCTTCATCCACTCCTTGGAGCTGGGTCACTCCGCTGCCACACGTGCCAT

CAAGGCGTCAGGTCCTGGCAGCAAGCGGCTGGGCATCGATGGCGACCGGGAGGCTGTTCCTCTAACACTACAG

ATTATTTACAGCCAGGGGCCATCAGTGGACGAAGTCGCTGGAGCAACCTGGAGAAGGTCTGTACCTCCGTGA

ACCTCAACAAGGCCTGCCGGAAGCAGGAGGAGCTGGATTCCAGCATGGAGGCCCTGACGCTAAACCTGACAGA

```
AGTGGTGAAAAGGCAGAACTCCAAATCCAAGAAGGGCTTTAACCAGATTAGCACATCGCAGATCAAAGTGGAC
AAGGTGCAGATCATCGGCTCCAACAGCTGCCCCTTTGCTGTGTGCCTGGACCAGGATGAGAGAAAGATCCTGC
AGAGTGTAGTCAGATGTGAGGTCTCACCGTGCTACAAGCCAGAGAAGAGCGACCTCTCCTCACCACCCCAGAC
GCCTCCTGACCTGCCGGCCCAGGCCGCACCTGATCTCTGCTCCCTCCTCTGCCTGCCCATCATGACTTTCAGT
GGAGCTCTGCCCTAGTGTGGGCCCAGCGCCAGACTGGACAGAAGCCCTGGGGTCATTTCTCCAGCACTAAAAT
GGAGTGGAGAGTTGGGGTGGAAATAAGACATCCTTAAAAGGTTAAATTGTCTGCAAAGCACCTAGCCCAGTGC
CGAGCTCCCAGTAGGTGTTCAGTAAAGCTTAGTGCCTGACTTTCTGAACACTGATTCCTCCTGTTTGGAGTCA
CTGGGATACTCTCATTGCCGTTGGGATGTTCCTCACTCCTTCCCAGTTCGTGGCTGAGGCAGAACCCAGACTG
AAGAGGGAAGAGACATTCCAGAGGAGGATTGCCTTCGTCAGGGTAAGGGGTGGGCTGCTCAGGGGCCCTACCC
TTCACCCCCTTCTGTATCAGATTGGCCCTCCCACTCCCATCTCACTCTGCGTGTACAATCTTCCATATCCGCA
AGTTCACTGGCACTCTTCTGGCACCTGGGCAAGATCCCAGAACAGAGGATGGAGTGACTGGCCTCACAGAGCT
TAGTGCCCGACACTGGTGCATGGGAAATGGTCAGCCTAGGATAGGACACGAGAGTCTGAAATTCAAAGCAACC
AGCTTGAAGTGGTTTGAGAAGCTGGAAGCAAACATGGGCTAGAGAGATAGGGCAGAAGTCAAGACGAGGATCT
GGACTGATGTGGAGAAAGTAGCCACGAAGCATGAACTGTATCCTGCACAAAGTCCCTCTTCCCCGCCTCCTA
ATTCATTATGCCCAAAAGGCCTTACGTGAAATTCCAGCCCAGAGTACTCATGACTTGAGAGACGTGGACAGAG
CCAGCTTCTACCTTGCCTGGCCGTCTCTCCCCTGTCTTAATGTCTGCTCTTGCTCTAAGCTCCAGAAGAGTGG
CGGGCCATGTATCTTCAATATGTTTTGCTGTATGGGCAGGTTGTCTTATTATGTGATCAACAGATGTCCAGG
AACTAATGAGTGGAATTTAATATTATTGTCAAATAAAACTTGATTTGTCCTAT
```

SEQ ID NO:4 - full-Length p101 protein

```
MQPGATTCTEDRIQHALERCLHGLSLSRRSTSWSAGLCLNCWSLQELVSRDPGHFLILLEQILQKTREVQEK
GTYDLLTPLALLFYSTVLCTPHFPPDSDLLLKAASTYHRFLTWPVPYCSICQELLTFIDAELKAPGISYQRL
VRAEQGLPIRSHRSSTVTVLLLNPVEVQAEFLAVANKLSTPGHSPHSAYTTLLLHAFQATFGAHCDVPGLHC
RLQAKTLAELEDIFTETAEAQELASGIGDAAEARRWLRTKLQAVGEKAGFPGVLDTAKPGKLHTIPIPVARC
YTYSWSQDSFDILQEILLKEQELLQPGILGDDEEEEEEEEEVEEDLETDGHCAERDSLLSTSSLASHDSTLS
LASSQASGPALSRHLLTSFVSGLSDGMDSGYVEDSEESSSEWPWRRGSQERRGHRRPGQKFIRIYKLFKSTS
QLVLRRDSRSLEGSSDTALPLRRAGSLCSPLDEPVSPPSRAQRSRSLPQPKLGTQLPSWLLAPASRPQRRRP
FLSGDEDPKASTLRVVVFGSDRISGKVARAYSNLRRLENNRPLLTRFFKLQFFYVPVKRSRGTSPGACPPPR
SQTPSPPTDSPRHASPGELGTTPWEESTNGISHYLGMLDPWYERNVLGLMHLPPEVLCQQSLKAEAQALEGS
PTQLPILADMLLYYCRFAARPVLLQVYQTELTFITGEKTTEIFIHSLELGHSAATRAIKASGPGSKRLGIDG
DREAVPLTLQIIYSQGAISGRSRWSNLEKVCTSVNLNKACRKQEELDSSMEALTLNLTEVVKRQNSKSKKGF
NQISTSQIKVDKVQIIGSNSCPFAVCLDQDERKILQSVVRCEVSPCYKPEKSDLSSPPQTPPDLPAQAAPDL
CSLLCLPIMTFSGALP
```

---

What is claimed is:

1. An expression vector comprising a polynucleotide capable of producing a polypeptide comprising the amino acid sequence of SEQ ID NO: 2 when said expression vector is present in a compatible host cell.

2. A process for producing a recombinant host cell which comprises the step of introducing an expression vector comprising a polynucleotide capable of producing a polypeptide comprising the amino acid sequence of SEQ ID NO: 2 into a cell such that the host cell, under appropriate culture conditions, produces said polypeptide.

3. A recombinant host cell produced by the process of claim 2.

4. A membrane of a recombinant host cell of claim 3 expressing said polypeptide.

5. A process for producing a polypeptide which comprises culturing a host cell of claim 3 under conditions sufficient for the production of said polypeptide and recovering said polypeptide from the culture.

6. The isolated polynucleotide comprising the nucleotide sequence set forth in SEQ ID NO:1.

7. An isolated polynucleotide comprising a polynucleotide sequence encoding a polypeptide which has at least 98% identity to the polypeptide sequence set forth in SEQ ID NO: 2 over the entire length of SEQ ID NO: 2, wherein said polypeptide has p101 regulatory activity towards phosphatidylinositol 3-kinase.

8. The isolated polynucleotide of claim 7 comprising a polynucleotide sequence encoding the polypeptide sequence set forth in SEQ ID NO: 2.

9. An isolated polynucleotide which is fully complementary to the polynucleotide in any one of claims 6–8 over the entire length of the polynucleotide set forth in such claim.

* * * * *